(12) United States Patent
Lin

(10) Patent No.: US 11,193,934 B2
(45) Date of Patent: *Dec. 7, 2021

(54) SAMPLE HEPATOCARCINOMA CLASSIFICATION WITH YKL-40 TO MASP2 CONCENTRATION RATIO

(75) Inventor: Biaoyang Lin, Hangzhou (CN)

(73) Assignee: Biaoyang Lin, Hangzhou (CN)

( * ) Notice: Subject to any disclaimer, the term of this patent is extended or adjusted under 35 U.S.C. 154(b) by 260 days.

This patent is subject to a terminal disclaimer.

(21) Appl. No.: 12/992,363

(22) PCT Filed: Oct. 20, 2008

(86) PCT No.: PCT/CN2008/001767
§ 371 (c)(1),
(2), (4) Date: Nov. 12, 2010

(87) PCT Pub. No.: WO2009/140805
PCT Pub. Date: Nov. 26, 2009

(65) Prior Publication Data
US 2011/0065120 A1    Mar. 17, 2011

(30) Foreign Application Priority Data

May 21, 2008 (CN) .......................... 200810108528.5

(51) Int. Cl.
*G01N 33/574* (2006.01)
(52) U.S. Cl.
CPC ... *G01N 33/574* (2013.01); *G01N 2333/4716* (2013.01); *G01N 2333/50* (2013.01)
(58) Field of Classification Search
CPC ............ C12Q 1/6886; C12Q 2600/158; G01N 33/574
See application file for complete search history.

(56) References Cited

U.S. PATENT DOCUMENTS

| 7,083,786 | B2 * | 8/2006 | Jensenius et al. | ......... 424/145.1 |
| 7,230,086 | B2 * | 6/2007 | Price et al. | ................ 530/388.1 |
| 7,939,263 | B2 * | 5/2011 | Clarke et al. | ................ 435/6.12 |
| 2003/0082652 | A1 | 5/2003 | Holten-Andersen et al. | |
| 2006/0019256 | A1 * | 1/2006 | Clarke et al. | ..................... 435/6 |
| 2007/0134681 | A1 * | 6/2007 | Liew et al. | ........................ 435/6 |

OTHER PUBLICATIONS

Lau et al. (Oncogene 2006, 25, 1242-1250).*
Segat et al. (Journal of Viral Hepatitis, 2008, 15, 387-391).*
Wang, Juan, et al. "Preparation and analysis of cSNP chip on hepatocellular carcinoma-related genes." Hepatobiliary Pancreat Dis Int 4.3 (2005): 398-402.*
Johansen, Julia S. "Studies on serum YKL-40 as a biomarker in diseases with inflammation, tissue remodelling, fibroses and cancer." Dan Med Bull 53.2 (2006): 172-209.*

* cited by examiner

*Primary Examiner* — G Steven Vanni
(74) *Attorney, Agent, or Firm* — Weisun Rao; Sunyong Tang; Venture Partner, LLC

(57) ABSTRACT

A method for increasing the veracity of classification by detecting protein YKL-40 and MASP2 levels in the samples, comprises detecting the content of the YKL-40 and MASP2 in the samples; the ratio of the content of YKL-40 to the that of MASP2 acted as variable, receiving the ROC curve according to the sensitivity and specialty of the difference threshold value to the diagnosis for the cancer, calculating an area under the curve AUC; classifying the samples according to the value of the AUC, sensitivity and specialty. And a kit for detecting the protein YKL-40 and MASP2 levels in the samples.

6 Claims, 2 Drawing Sheets

Drawings of Specification

SAMPLE HEPATOCARCINOMA CLASSIFICATION WITH YKL-40 TO MASP2 CONCENTRATION RATIO

CROSS REFERENCE TO RELATED APPLICATIONS

This application is a national phase application and claims the benefit, under 35 U.S.C. § 371, of PCT/CN2008/001767, filed on Oct. 20, 2008, which in turn claims the priority of Chinese Patent Application No. 200810108528.5, filed on May 21, 2008. Both applications are incorporated herein by reference in their entireties.

TECHNICAL FIELD

The present invention pertains to the technical field of biomedicine. Specifically, the present invention relates to a method to improve the accuracy of sample classification and a reagent kit used to detect YKL-40 and MASP2 proteins in the samples.

BACKGROUND ART

Hepatocarcinoma (HCC) is a frequently-encountered and lethal malignant tumor. According to statistics, the number of HCC patients increases by about 500,000 and about 500,000 patients die of this disease annually (Parkin, D. M., Bray, F., Ferlay, J., and Pisani, P.b(2001) Estimating the world cancer burden: Globocan 2000.Int J Cancer 94, 153-1 56.). The current approaches for the diagnosis of HCC include ultrasonic detection and Alpha.Fetoprotein (AFP) detection, which are usually used together (Spangenberg, H. C., Thimme, R., and Blum, H. E. (2006) Serum markers of hepatocellular carcinoma. Semin Liver Dis 26, 385-390,) when AFP is used as the biomarker for HCC diagnosis through the ROC curve, the positive threshold of detection is usually 20 ng/ml (See: Chen Jiwu and Fan Peichang. Prepacontentn of an immunochromatographic strip for quick AFP detection. Journal of Analytical Science. Issue 4, 2002, 273.276). The sensitivity and specificity of ultrasonic-AFP joint detection are respectively 50-85% and 70-90%. But its false positive and false negative rate is high up to 40% (Tu, D. G., Wang, S. T, Chang, T. T., Chiu, N. T., and Yao, W. J.(1 999) The value of serum tissue polypeptide specific antigen in the diagnosis of hepatocellular carcinoma. Cancer 85, 1039-1043; Buscarini, L., Sbolli, G., Cavanna, L., Civardi, G., Di Stasi, M., Buscarini, E., and Fomari, F.(1 987) Clinical and diagnostic features of 67 cases of hepatocellular carcinoma. Oncology 44, 93.97.). Therefore people urgently need scientific researchers to develop an HCC diagnosis approach which provides easier detection, higher sensitivity and specificity, and higher accuracy.

YKL-40 is an abbreviation of human cartilage glycoprotein 39 (HcGP.39) or chitinase 3-like 1 (which is abbreviated as CHI3L1). Research has revealed that the level of YKL-40 in Serum is related to many disease conditions such as osteoarthritis, primary colorectal carcinoma, breast carcinoma, and recurrent oophoroma and can be used for the diagnosis, prognosis evaluation, and monitoring of treatment effect and disease progression of some diseases. For example, it can be used for the diagnosis and prognosis of oophoroma (see, e.g., M. Cheng et al., Application of serum YKL-40 in the diagnosis and prognosis of oophoroma patients, *Guangdong Medical Journal*, 2008, 29(2): 255-256). in an essay published in the *New England Journal of Medicine* on Nov. 15, 2007, researchers of Yale School of Medicine stated that results of clinical experiments indicated that this molecule may play an important role in the determination of the physiological reactions to severe asthma. Compared with normal people, asthma patients have more YKL-40-circulating serum, which is also related to the severity of asthma. Johansen et al. of the University of California at San Diego stated that YKL-40 is a biomarker independent of carcinoembryonic antigen (CEA) and lactin dehydrogenase (LDH), normal people having high levels of YKL-40 are exposed to 2.7 times as much risk of gastrointestinal tumor as others and usually have poor prognosis after being diagnosed as having gastrointestinal tumor. It has also been discovered that the level of serum YKL-40 can be used as an indicator of hepatic fibrosis (see,e.g., J.S. Johansen, P. Christoffersen, S. Moiler, P.A. Price, J.H. Henriksen, C. Garbarsch, and F. Bendtsen, Serum YKL-40 is increased in patients with hepatic fibrosis, *Journal of Hepatology*, 2000: 32, 911-920). However, there have not been reports about the application of YKL-40 detection in HCC diagnosis.

MASP2 is the abbreviation of mannan-binding lectin associated serine protease-2. It is related to human immunodeficiency diseases and plays an important role in the innate immune defense of the organism (See: Cai Xuemin et. al. Prokaryotic expression of mannan-binding lectin associated serine protease-2 in N-end segments. Journal of Immunology. 2007 (03) 235-238). But no report has been published about its application in HCC diagnosis.

Research by the Inventor has revealed that MASP2 gene is a gene specifically expressed in the liver. Through a lot of research, the Inventor accidentally found that both proteins are related to the symptoms of HCC. Blood serum of HCC patients has significantly higher level of YKL-40 than normal samples. And the expression of MASP2 is lower in HCC patients than in normal samples. Therefore we hereby propose an hypothesis: By combining a protein having high expression in carcinoma (this protein may be not specific to a certain carcinoma and may be highly expressed in different types of carcinoma) with a protein having low expression in a specific tissue or organ (down-regulation of the specific protein executing specific functions of the tissue or organ due to the carcinoma), we can obtain a joint biomarker for cancer diagnosis. This joint marker will improve the sensitivity and specificity of cancer detection. We take YKL-40 and MASP2 proteins as examples to check if they can be used as a biomarker for the clinical application to HCC and if their joint detection can improve the accuracy of diagnosis and prognosis of the disease.

CONTENTS OF THE INVENTION

Based on the findings described above, the primary purpose of the invention is to provide a method to improve the accuracy of sample classification through joint-detection of YKL40 and MASP2 proteins in the sample.

A further purpose of the invention is to provide a reagent kit for the detection of YKL40 and MASP2 proteins in the sample.

A further purpose of the invention is to provide a method to improve the sensitivity of sample analysis through joint-detection of carcinoma high expression protein and tissue or organ specific expression protein in the sample.

A further purpose of the invention is to provide a reagent kit used for the detection of carcinoma high expression protein and tissue or organ specific expression protein in the sample.

In accordance with the present invention, the following technical approaches are disclosed which address the purposes described above:

A method to improve the accuracy of sample classification, characterized in the joint detection of Proteins YKL-40 and MASP2 in the sample.

The joint detection mentioned above comprises:
(1) Detection of the YKL-40 and MASP2 concentrations in sample;
(2) Algorithmic analysis of the measured YKL-40 and MASP2 concentrations, and
(3) Classification of the test sample according to the algorithmic analysis results.

The application of the method described above in the diagnosis, prognosis evaluation, and monitoring of treatment effect and disease course of cancer.

A reagent kit used for the detection of YKL40 and MASP2 proteins in the sample, comprising:
(1) Antibodies capable of binding YKL40 and MASP2, and
(2) Marked antibodies capable of binding YKL40 and MASP2 when YKL40 and/or MASP2 are bound by antibodies stated in (1).

A method to improve the sensitive of cancer detection of the individual, comprising:
(1) Measurement of the concentration of carcinoma high expression protein in the sample of the individual;
(2) Measurement of the concentration of specifically expressed protein in a certain tissue or organ in the sample of the individual;
(3) Algorithmic analysis of the measured carcinoma high expression protein and tissue or organic specific expression protein, and
(4) Classification of the individual as having cancer or being healthy according to the algorithmic analysis results.

A reagent kit used for the detection of carcinoma high expression protein and tissue or organ specific expression protein in the sample, comprising:
(1) Antibodies capable of binding carcinoma high expression protein and tissue or organ specific expression protein, and
(2) Marked antibodies capable of binding the carcinoma high expression protein and tissue or organ specific expression protein when the carcinoma high expression protein and/or tissue or organ specific expression protein are bound by the antibodies stated in (1).

Research has revealed that by using the method and reagent kit of the present invention for the joint detection of YKL40 protein and MASP2 protein in the sample of the individual, we can effectively raise the sensitivity, specificity, and accuracy of cancer diagnosis. And the invention can be extended to the diagnosis, prognosis evaluation, evaluation of treatment effect, and monitoring of disease course of many other diseases.

DESCRIPTION OF ATTACHED DRAWINGS

DETAILED DESCRIPTION OF THE INVENTION

Figure 1:
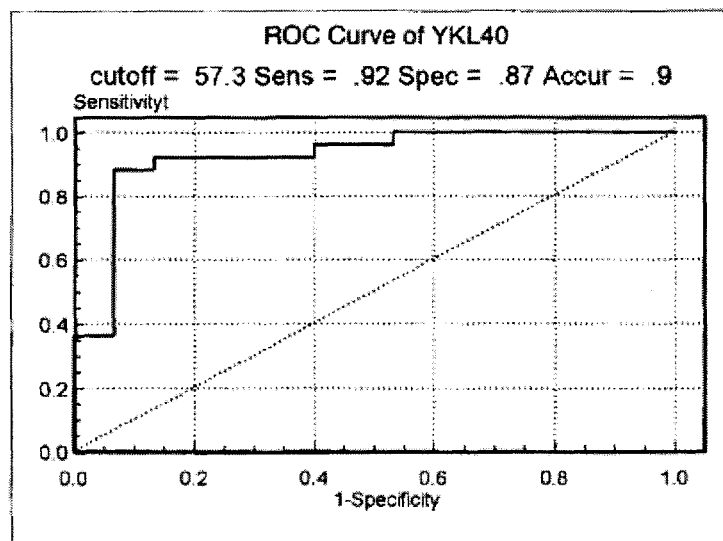
FIG. 1 is the ROC curve of the detection of YKL-40 in the serum sample of an HCC patient.

The present invention will be further described with detailed embodiments and attached drawings. It is to be expressly understood that the following embodiments are set forth as examples and not by way of limitations on the invention as ultimately defined in the claims.

It is known to all that when an individual is afflicted by cancer or is in the clinical stage of cancer, the virus or genes of the cancer will be highly expressed. Such highly expressed proteins, such as YKL-40, can be used as biological markers of cancer. On the other hand, functions of related tissues or organs of the individual will decline, resulting in reduced levels of proteins which are specifically expressed in such tissues or organs, such as MASP2 specifically expressed in the liver. Therefore the low expression levels of proteins specifically expressed in tissues or organs also have the potential to serve as biological markers of cancer. It is well known by those having ordinary skill in the art that tests with a single biological marker may sometimes cause false positive or false negative increases and thus reduce the accuracy of TN test. Therefore both the concentrations of carcinoma high expression proteins in the sample of the individual, such as YKL-40, and the low expression levels of proteins specifically expressed in certain tissues or organs, such as MASP2 which is specifically expressed in the liver, are measured at the same time. In other words, new markers are added on the basis of original pairing markers in order to improve the sensitivity of the detection. This method will raise the sensitivity of cancer tests. And it will be verified in the following embodiments.

It is beyond doubt that the method and corresponding reagent kit used by the present invention to improve the sensitivity of cancer detection of individuals can be applied to the diagnosis, prognosis evaluation, evaluation of treatment effect, and monitoring of disease course of all kinds of cancer and pathogenic changes in the organs.

Let's take joint detection of blood samples for example. The application of the invention to the cancer or disease of a specific tissue or organ comprises the following steps: Assay of high-level expression proteins or genes of cancer or disease in the blood sample of the individual; Assay of low-level expression of tissue-specific or organ-specific proteins or genes in blood; Algorithmic analysis of the measured protein concentration or gene expression results; and classification of the measured sample of the individual according to the algorithmic analysis results in order to obtain diagnosis result of the cancer or disease. The result may be: healthy, early-stage cancer or disease, mid-term cancer or disease, or terminal cancer or disease.

It should be understood that the term "joint detection" in this Specification: not only comprises the measurement of the concentrations of specific proteins in the sample, but also comprises the algorithmic analysis of the measured protein concentrations. And it further comprises the classification of the test sample according to the results of algorithmic analysis.

ELISA

The ELISA technology is used in the present invention for the detection of carcinoma high expression proteins, such as YKL40, and tissue or organ specific expression proteins, such as MASP2, in the sample of the individual.

ELISA (enzyme linked immunosorbent assay) is a commonly-used protein concentration analysis method in molecular biology. It can be used to measure both antigens and antibodies. Many other types of assay can be adopted in the present invention according to the source of reagent, characters of the sample, and the detection conditions, such as: Double antibody sandwich method, two-site one-step method, and indirect method for the assay of antibodies, competition method and capture method for the assay of IgM antibody, and ELISA with the use of avidin and biotin.

The Reagent Kit

A reagent kit is preferred for the ELISA of the present invention as it can realize quick operation and avoid the complicated and troublesome routine experimental detection. The ELISA kit of the present invention comprises a YKL40 immunoenzymatic standard kit, a MASP2 immunoenzymatic standard kit, and YKL40 and MASP2 detection kits. YKL40 and MASP2 detection kits are preferred in order to improve the sensitivity, specificity, and accuracy of disease diagnosis. They can be used respectively or simultaneous to measure two groups of detection results in order to provide quick effects.

The YKL40 and MASP2 detection kits of the present invent shall at least comprise:
(1) Antibodies capable of binding YKL40 and MASP2; and
(2) Marked antibodies capable of binding YKL40 and MASP2 when YKL40 and/or MASP2 are bound by antibodies stated in (1).

The reagent kits mentioned above may further comprise:
(3) Standard samples composed of solutions containing known amounts of YKL40 and MASP2, which may come from the bacterial expression of gene engineering, animals, or human body fluid, and
(4) Antibody markers, such as enzyme labels like horse radish peroxidase or fluorescent marks in the reported methods, which can bind antibodies to form conjugates for detection.

A more preferred kit may further comprise at least one of the following articles: (5) A carrying tool, whose space is divided into compartments to hold one or several vessels, 96-pore plates, or strips, wherein the vessels may be vials, test tubes, and similar articles and each vessel contains an independent component used in the method of the present invention; (6) Auxiliary reagents, such as color development reagent, enzyme inhibitor, buffer solutions, stabilizing agent, diluting agent, rinsing reagent, and similar reagents; (7) Instructions of use which may be written on vials, test tubes, and similar articles, or on a separate piece of paper, or outside or inside the vessels, or in the form of multimedia such as CD, computer compact disc, or video.

Preferred antibodies can be fixed on solid-state carriers to form capture antibodies.

The antibodies comprise any antibody segments capable of binding YKL40 and MASP2 and may be recombinants, chimeric antibodies, humanized antibodies, and murine antibodies. Said antibodies may be monoclonal antibodies or polyclonal antibodies. Monoclonal antibodies are preferred.

The preferred antibody conjugate can be put to photometry with ELISA readers such as ELIASA.

Samples

Samples used by the present invention can include multiple forms, such as whole blood, blood plasma, blood serum, urine, cerebrospinal fluid, saliva, or tear. Blood serum is preferred.

Sample preparation can be done with normal methods such as centrifugation, such as in the following references: Young, D. S. & Bermes, E. W. "Specimen collection and processing" in Tietz Textbook of Clinical Chemistry 2nd Edition" Eds. Burtis, C. A. & Ashwood, E. R., Saunders (1994); Methods in Enzymology, H. Van Vunakis and J. J. Langone (Eds), 1981, 72(B); Practice and Theory of Enzyme Immunoassays, P Tijssen, Laboratory Techniques in Biochemistry and Molecular Biology, R. J. Burden and P. H. Van Knippenberg (Eds), Elsevier, 1985; Introduction to Radioimmunoassay and Related Techniques, T. Chard, ibid, 3rd Edition, 1987; Methods in Enzymology, H. Van Vunakis and J. J. Langone (Eds) 1981, 74(C).

ROC Curve

After using ELISA to measure the concentrations of carcinoma high expression proteins, such as YKL40, and tissue or organ specific expression proteins, such as MASP2, in the sample, we can use algorithmic analysis for the statistic treatment of the measured concentrations of carcinoma high expression proteins, such as YKL40, and tissue or organ specific expression proteins, such as MASP2 in the sample, and thus obtain a classification standard having significance for sample classification. This algorithmic method is preferably done with a computer. For example the data can be used to draw an ROC curve and then to classify the sample of the individual.

The full name of ROC curve is receiver operator characteristic curve, which is also known as receiver operation characteristic curve. It is mainly used for clinical biochemical diagnostic tests. ROC curve is a comprehensive indicator the reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high.

The ROC curve evaluation method is different from the traditional evaluation methods in that intermediate states are allowed in accordance with the actual situation. The test results can be divided into several ordered classes such as: normal, basically normal, suspicious, basically abnormal, and abnormal.

When it comes to the diagnosis of diseases, the ordered classes mentioned above can be divided into: negative, uncertain, and positive. When it comes to the diagnosis of diseases, the ordered classes mentioned above can be further divided into: cancer and healthy.

Therefore according to the example of the detection of YKL40 and MASP2 proteins in the sample, the method of the present invention to improve the accuracy of sample classification may comprise the following steps:
(1) Respectively determine the YKL-40 and MASP2 concentrations in the sample;
(2) Draw an ROC curve with the ratio between YKL40 concentration and MASP2 concentration as the variable according to the sensitivity and specificity values of different thresholds to the diagnosis of cancer, and then calculate the area under the curve (AUC), and
(3) Classify the test sample according to the expected sensitivity and specificity (cancer or healthy).

Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CRE- ATE—ROC.SAS, GB STAT VI0.0 (Dynamic Microsystems, Inc. Silver Spring, Md., USA), etc.

Diagnosis, Prognosis Evaluation and Monitoring of Treatment Effect or Disease Course of HCC The specific application of the present invention in the field of medicine is mainly focused on the diagnosis, prognosis evaluation, and monitoring of treatment effect of disease course of HCC, comprising the operating method and the tool to realize the method—the reagent kit. It is known to all that the disease course of hepatitis is closely related to the conversion to HCC. The typical disease course is: Hepatitis (e.g. hepatitis B or hepatitis C)—cirrhosis—HCC. Research by the inventor has already revealed that the expression of hepatitis virus can also be used as a biological marker for HCC detection. And combining the expressions of YKL40 and MASP2 for joint detection can significantly improve the success ratio of HCC diagnosis. For this sake, the present invention further provides a method for the diagnosis, prognosis evaluation, and monitoring of treatment effect or disease course of hepatocarcinoma, comprising: detection of the expression of hepatitis virus in the blood sample of the individual; detection of the expression of YKL40 and MASP2 in the blood sample of the individual; algorithmic analysis of the measured expression levels of hepatitis virus and YKL40 and MASP2; and classification of the measured blood sample according to the algorithmic analysis results in order to obtain the judgment result of HCC. The result may be: early-stage HCC, mid-term HCC, or terminal HCC.

The expression of hepatitis virus can be done with the standard methods in the art, such as standard blood sample test paper method, blood sample reagent kit method, and routine blood sample test method, etc.

It is obvious that integrating the expression of hepatitis virus, YKL40 and MASP2 of blood sample into the same reagent kit will make HCC detection more convenient, time-efficient, and economical. For this sake, the present invention further provides a joint-test kit for the diagnosis, prognosis evaluation, and monitoring of treatment effect or disease course of HCC, which at least comprises: (1) Antibodies capable of binding hepatitis virus, YKL40 and MASP2, and (2) Marked antibodies capable of binding hepatitis virus and/or YKL40 and MASP2 YKL40 when hepatitis virus and/or YKL40 and/or MASP2 are bound by antibodies stated in (1). The preferred reagent kit may further comprise: (3) Standard samples composed of solutions containing known amounts of hepatitis virus, YKL40 and MASP2, which may come from the bacterial expression of gene engineering, animals, or human body fluid, and (4) Antibody markers, such as enzyme labels like horse radish peroxidase or fluorescent marks in the reported methods, which can bind antibodies to form conjugates for detection.

The present invention will be further described in detain with the example of the HCC diagnosis of individual blood serum as the sample.

EMBODIMENT 1

Sample Collection 1 mL blood serum is taken from each of the 25 cases of HCC patients aged 50-60 at No. 1 Affiliated Hospital of Zhejiang University School of Medicine as the positive control. 1 mL normal blood serum is taken from each of the 15 cases of healthy volunteers aged 50-60 for YKL40 and MASP2 concentration test.

Measurement of YKL-40 Concentration

A YKL-40 kit produced by Quidel Company (San Diego, Calif., USA) and a Bio-Rad 680 ELIASA (US) are used for ELISA operation in accordance with the manufacturer's instructions. The operation comprises:

1. Allow pouch of Coated Strips to equilibrate to 18-28° C. before opening. Remove Stripwell Frame and the required number of Coated Strips from the pouch. Ensure that the pouch containing unused strips is completely resealed and contains desiccant. The total number of specimens to be tested and the number of specimens for quality control were calculated. Each specimen needed one antigen-coated well and three replicates were performed for each sample.
2. Place desired number of Coated Strips in Stripwell Frame.
3. Add 20 μL Standard, Control, or sample to each well of the Coated Strips. This step was completed within 30 minutes.
4. Add 100 μL of Capture Solution to each well. Dispense Capture Solution with sufficient force to ensure adequate mixing. Tap Stripwell Frame several times.
5. Incubate 60±5 minutes at 18-28° C.
6. Manually invert/empty strips. Add at least 250 μL of 1× Wash Buffer to each well and manually invert/empty strips. Repeat three more times for a total of four washes. Vigorously blot the strips dry on paper towels after the last wash.
7. Add 100 μL of reconstituted Enzyme Conjugate to each well. Discard remaining reconstituted Enzyme Conjugate after use.
8. Incubate 60±5 minutes at 18-28° C.
9. Repeat wash as indicated in step 6.
10. Add 100 μL of Working Substrate Solution to each well.
11. Incubate for 60±5 minutes at 18-28° C.
12. Add 100 μL of Stop Solution to each well. Add Stop Solution in the same pattern and time intervals as the Working Substrate Solution addition.
13. Read the optical density at 405 nm. Assure that no large bubbles are present in wells and that the bottom of the strips are clean. Strips should be read within 15 minutes of Stop Solution addition.
14. using a linear calibration curve "Y=mx+b" to analyze the result of YKL-40 or MASP2;
15. using the standard curve to read the concentrations of YKL-40 or MASP2 in the blood serum sample or control solution.

Results

Table 1 shows the detection results obtained through the steps described above.

TABLE 1

| Sample No. | Diagnosis result | Protein concentration in serum (ng/mL) | | YKL-40/ MASP-2 ratio |
|---|---|---|---|---|
| | | YKL-40 | MASP-2 | |
| 1 | HCC | 782.2 | 1359.9 | 57.52 |
| 2 | HCC | 76.8 | 250.2 | 30.7 |
| 3 | HCC | 705 | 195.7 | 360.25 |
| 4 | HCC | 1444.6 | 90.3 | 1599.78 |
| 5 | HCC | 165.3 | 281.75 | 58.67 |
| 6 | HCC | 98.7 | 248.4 | 39.73 |
| 7 | HCC | 317.2 | 58.5 | 542.22 |
| 8 | HCC | 354.1 | 81.6 | 433.95 |
| 9 | HCC | 211.7 | 167.2 | 126.61 |
| 10 | HCC | 87.8 | 33.9 | 259 |

TABLE 1-continued

| Sample No. | Diagnosis result | Protein concentration in serum (ng/mL) | | YKL-40/ MASP-2 ratio |
|---|---|---|---|---|
| | | YKL-40 | MASP-2 | |
| 11 | HCC | 734.4 | 292.9 | 250.73 |
| 12 | HCC | 184.4 | 935.9 | 19.7 |
| 13 | HCC | 94.6 | 206.4 | 45.83 |
| 14 | HCC | 313 | 208.3 | 150.26 |
| 15 | HCC | 137.3 | 124.7 | 110.1 |
| 16 | HCC | 475.3 | 241.6 | 196.73 |
| 17 | HCC | 66.5 | 282.7 | 23.52 |
| 18 | HCC | 177.62 | 244.54 | 72.63 |
| 19 | HCC | 59.96 | 426.67 | 14.05 |
| 20 | HCC | 44.96 | 80.29 | 56 |
| 21 | HCC | 99.9 | 630.05 | 15.86 |
| 22 | HCC | 115.68 | 215.56 | 53.66 |
| 23 | HCC | 183.47 | 339.71 | 54.01 |
| 24 | HCC | 440.81 | 106.86 | 412.51 |
| 25 | HCC | 36.09 | 244.06 | 14.79 |
| 26 | Healthy | 34.4 | 185 | 18.59 |
| 27 | Healthy | 21.5 | 171 | 12.57 |
| 28 | Healthy | 57.3 | 724 | 7.91 |
| 29 | Healthy | 54 | 443.9 | 12.16 |
| 30 | Healthy | 62.9 | 356.2 | 17.66 |
| 31 | Healthy | 47.5 | 330.7 | 14.36 |
| 32 | Healthy | 25.8 | 699.9 | 3.69 |
| 33 | Healthy | 43.8 | 837.7 | 5.23 |
| 34 | Healthy | 48.5 | 470.5 | 10.31 |
| 35 | Healthy | 16.7 | 384.2 | 4.35 |
| 36 | Healthy | 14.8 | 739.4 | 2 |
| 37 | Healthy | 39.6 | 469.4 | 8.44 |
| 38 | Healthy | 11 | 363.2 | 3.03 |
| 39 | Healthy | 10.4 | 330.1 | 3.15 |
| 40 | Healthy | 265.8 | 530.1 | 50.14 |

From Table 1 We can see that the concentration of MASP2 is also closely correlated to the symptoms of HCC. In other Words, the concentration of MASP2 protein in the blood serum of HCC patients is significantly lower than the concentration of MASP2 protein in the blood serum of healthy volunteers.

Drawing ROC Curve

AGB STAT V 10.0 (Dynamic Microsystems, Inc. Silver Spring, Md. USA) system is used to draw the ROC curve with the concentration of YKL40 protein as the variable according to the sensitivity and specificity values of different thresholds to the diagnosis of cancer, and then to calculate the area under the curve (AUC). The ROC curve and calculation of AUC are shown in FIG. 1.

FIG. 1 shows that the AUC of the ROC curve is 0.98. When the threshold value of the concentration of YKL-40 is 0.87 (ng/mL), the sensitivity of HCC diagnosis is 0.92 (i.e. 92%), the 1-specificity is 0.87 (i.e. 87%), and the success ratio of HCC diagnosis is 0.9 (i.e. 90%).

EMBODIMENT 2

Measurement of MASP2 Concentration

Similar steps to those of Embodiment 1 are used. They are different in that: The concentration of MASP2 protein in blood serum sample is measured with a MASP2 kit produced by Dutch Hycult Biotechnology Company (Uden, Holland) is used for ELISA operation according to the manufacturer's instructions. The results are shown in Table 1.

From Table 1 we can see that the concentration of MASP2 is also closely correlated to the symptoms of HCC. In other words, the concentration of MASP2 protein in the blood serum of HCC patients is significantly higher than the concentration of MASP2 protein in the blood serum of healthy volunteers.

Drawing ROC Curve

Figure 2:
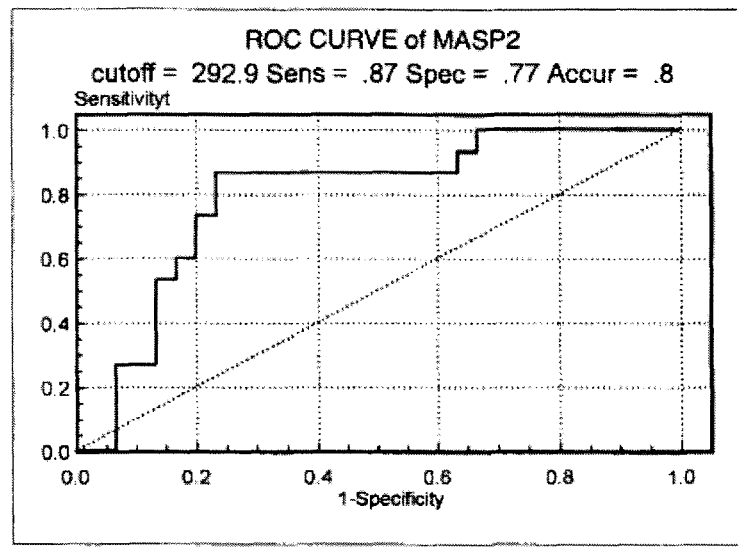
FIG. 2 is the ROC curve of the detection of MASP2 in the serum sample of an HCC patient.

A GB STAT V10.0 system is used to draw an ROC curve with the concentration of MASP2 protein as the variable according to the sensitivity and specificity values of different thresholds to the diagnosis of cancer, and then to calculate the area under the curve (AUC), as shown in FIG. 2.

FIG. 2 shows that when the threshold value of the concentration of MASP2 is 292.9 (ng/mL), the sensitivity of HCC diagnosis is 0.87, the 1-specificity is 0.77 (i.e. 87%), and the actual success ratio of HCC diagnosis is 0.8.

EMBODIMENT 3

YKL40 and MASP2 are combined. In other words, the GB STAT V10.0 system is used to draw an ROC curve with the ratio between the concentration of YKL40 protein and the concentration of MASP2 protein as the variable according to the sensitivity and specificity values of different thresholds to the diagnosis of cancer, and then to calculate the area under the curve (AUC), as shown in FIG. 3.

Figure 3:
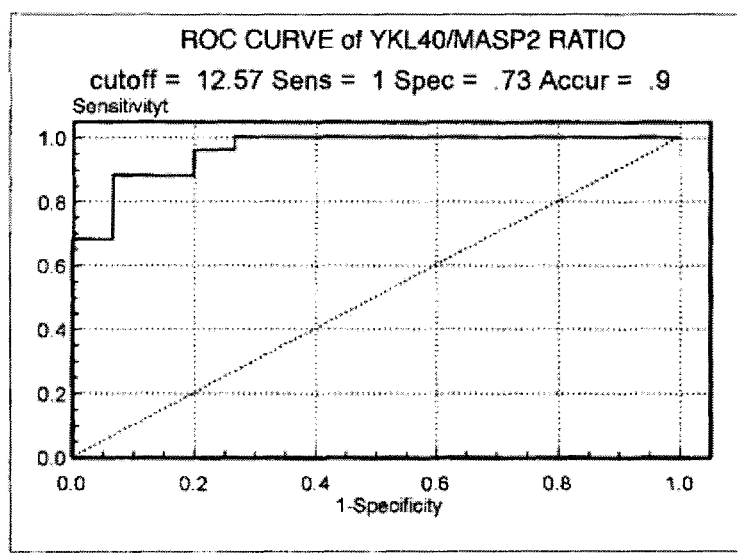
FIG. 3 is the ROC curve of the joint detection of both YKL40 and MASP2 in the serum sample of an HCC patient.

FIG. 3 shows that when the threshold value is 12.57 (ratio), the sensitivity of HCC diagnosis is 100% and the actual success ratio of HCC diagnosis is 90%. The success ratio is far greater than that (usually 70%) of AFP detection which is being commonly used today.

In addition, by comparing FIG. 3, FIG. 1, and FIG. 2 we can see that when the threshold is 12.57, the sensitivity of HCC diagnosis under joint detection of YKL40 and MASP2 is higher than that of any single marker (the sensitivity under joint detection is 1, and the sensitivity values of single YKL40 and MASP2 are respectively 0.92 and 0.87) and the actual success ratio of HCC diagnosis is 0.9.

The technical solution of the present invention has been explained with the example of HCC diagnosis above, wherein an independent YKL40 or MASP2 kit is used for ELISA operation and the ROC curve of joint detection of YKL40 and MASP2 is drawn. However, in accordance with the disclosure of the present invention, the method of the invent can absolutely be extended to the diagnosis, prognosis evaluation, and monitoring of treatment effect and development of some other diseases, which is obvious to those having ordinary skill in the art. Therefore, alterations and modifications may be made by those having ordinary skill in the art without departing from the spirit and scope of the invention, and such alterations and modifications are also defined to be within the scope of the invention.

The invention claimed is:

1. A method for classifying a sample into an HCC category or a normal category, comprising:
   i). obtaining a predetermined threshold YKL-40/MASP2 value or a threshold YKL-40/MASP-2 ratio, which comprises:
      (1) obtaining multiple samples with known categories, wherein the multiple samples have been diagnosed to be in the HCC category or the normal category,
      (2) measuring YKL-40 and MASP2 concentrations in each sample of the multiple samples with antibodies that capture YKL-40 and MASP2 respectively,
      (3) calculating a YKL-40/MASP2 value using statistical analysis based on the measured YKL-40 concentration and the measured MASP2 concentration, or a YKL-40/MASP2 ratio by dividing the measured YKL-40 concentration with the measured MASP2 concentration for each sample, (4) drawing a ROC curve using the YKL-40/MASP2 values or the YKL-40/MASP2 ratios as a variable and the known categories as another variable from the multiple samples, and (5) determining a threshold YKL-40/MASP2 value or a threshold YKL-40/MASP2 ratio for classifying a sample into the HCC category or the normal category based on a desired sensitivity and specificity;

ii). determining whether a sample is in the HCC category, which comprises:
(1) obtaining the sample from a patient,
(2) measuring YKL-40 and MASP2 concentrations in the sample with antibodies that capture YKL-40 and MASP2 respectively, wherein YKL-40 is a protein with a higher expression in hepatocellular carcinoma compared to normal samples and MASP2 is a protein with a lower expression in hepatocellular carcinoma compared to normal samples,
(3) calculating a YKL-40/MASP2 value using statistical analysis based on the measured YKL-40 concentration and the measured MASP2 concentration or a YKL-40/MASP2 ratio by dividing the measured YKL-40 concentration with the measured MASP2 concentration, and
(4) classifying the sample into the HCC category if the YKL-40/MASP2 value is greater than the predetermined threshold YKL-40/MASP2 value or if the YKL-40/MASP2 ratio is greater than the predetermined threshold YKL-40/MASP2 ratio; otherwise, classifying the sample into the normal category.

2. The method according to claim 1, wherein at least one of the YKL-40 and MASP2 concentrations is measured with any antibody capture assay such as the ELISA technology.

3. The method according to claim 1, wherein the sample is selected from a group consisting of whole blood, blood plasma, blood serum, urine, cerebrospinal fluid, saliva, and tears.

4. A method for diagnosis, prognosis, and monitoring of treatment effect or disease course of HCC of an individual to be in an HCC category or a normal category, comprising:
i). obtaining a predetermined threshold YKL-40/MASP2 value or a threshold YKL-40/MASP2 ratio, which comprises:
(1) obtaining multiple samples with known categories, wherein the multiple samples have been diagnosed to be in the HCC category or the normal category,
(2) measuring YKL-40 and MASP2 concentrations in each sample of the multiple samples with antibodies that capture YKL-40 and MASP2 respectively,
(3) calculating a YKL-40/MASP2 value using statistical analysis based on the measured YKL-40 concentration and the measured MASP2 concentration, or a YKL-40/MASP2 ratio by dividing the measured YKL-40 concentration with the measured MASP2 concentration for each sample,
(4) drawing a ROC curve using the YKL-40/MASP2 values or the YKL-40/MASP2 ratios as a variable and the known categories as another variable from the multiple samples, and
(5) determining a threshold YKL-40/MASP2 value or a threshold YKL-40/MASP2 ratio for classifying a sample into the HCC category or the normal category based on a desired sensitivity and specificity;

ii). determining whether the individual has HCC, which comprises:
(1) obtaining a blood sample from the individual,
(2) conducting an assay of a protein with a higher level of expression in hepatocellular carcinoma compared to normal samples, comprising measuring YKL-40 concentration in the blood sample of the individual;
(3) conducting an assay of a protein with a lower level of expression in hepatocellular carcinoma compared to the normal samples, comprising measuring MASP2 concentration in the blood sample of the individual;
(4) calculating a YKL-40/MASP2 value using standard statistical analysis based on the measured YKL-40 concentration and the measured MASP2 concentration or a YKL-40/MASP2 ratio by dividing the measured YKL-40 concentration with the measured MASP2 concentration; and
(5) determining the individual is in the HCC category if the YKL-40/MASP2 value is greater than the predetermined threshold YKL-40/MASP2 value or if the YKL-40/MASP2 ratio is greater than the predetermined threshold YKL-40/MASP2 ratio; otherwise, determining the individual is in the normal category.

5. A method for diagnosing and treating hepatocellular carcinoma in a subject in need thereof, comprising:
diagnosing presence of hepatocellular carcinoma in the subject which comprises:
i). obtaining a predetermined threshold YKL-40/MASP2 value or a threshold YKL-40/MASP2 ratio, which comprises:
(1) obtaining multiple samples with known categories, wherein the multiple samples have been diagnosed to be in the hepatocellular carcinoma category or the normal category,
(2) measuring YKL-40 and MASP2 concentrations in each sample of the multiple samples with antibodies that capture YKL-40 and MASP2 respectively,
(3) calculating a YKL-40/MASP2 value using statistical analysis based on the measured YKL-40 concentration and the measured MASP2 concentration, or a YKL-40/MASP2 ratio by dividing the measured YKL-40 concentration with the measured MASP2 concentration for each sample,
(4) drawing a ROC curve using the YKL-40/MASP2 values or the YKL-40/MASP2 ratios as a variable and the known categories as another variable from the multiple samples, and
(5) determining a threshold YKL-40/MASP2 value or a threshold YKL-40/MASP2 ratio for classifying a sample into the hepatocellular carcinoma category or the normal category based on a desired sensitivity and specificity;

ii). determine whether the subject has hepatocellular carcinoma, which comprises:
(1) obtaining a sample from the subject,
(2) measuring YKL-40 and MASP2 concentrations in the sample with antibodies that capture YKL-40 and MASP2 respectively, wherein YKL-40 is a protein with a higher expression in hepatocellular carcinoma compared to normal samples and MASP2 is a protein with a lower expression in hepatocellular carcinoma compared to normal samples,
(3) calculating a YKL-40/MASP2 value using statistical analysis based on the measured YKL-40 concentration and the measured MASP2 concentration or YKL-40/MASP2 ratio by dividing the measured YKL-40 concentration with the measured MASP2 concentration, and
(4) determining the subject has hepatocellular carcinoma if the YKL-40/MASP2 value is greater than the predetermined threshold YKL-40/MASP2 value or if the YKL-40/MASP2 ratio is greater than the predetermined threshold YKL-40/MASP2 ratio; and administering to the subject determined as having hepatocellular carcinoma a drug that is effective in treating hepatocellular carcinoma.

6. The method of claim 5, wherein the sample is selected from a group consisting of whole blood, blood plasma, blood serum, urine, cerebrospinal fluid, saliva, and tears.

* * * * *